United States Patent [19]

Bartley

[11] Patent Number: 5,189,004
[45] Date of Patent: Feb. 23, 1993

[54] ALKENYL ALKANOATE CATALYST PROCESS

[75] Inventor: William J. Bartley, Charleston, W. Va.

[73] Assignee: Union Carbide Chemicals & Plastics Technology Corporation, Danbury, Conn.

[21] Appl. No.: 793,127

[22] Filed: Nov. 18, 1991

[51] Int. Cl.$^5$ .................. B01J 37/03; B01J 31/28; B01J 23/58; B01J 23/66
[52] U.S. Cl. .................. 502/170; 502/330; 560/245; 560/241.1
[58] Field of Search .............. 502/170, 330; 560/245, 560/241.1

[56] References Cited

U.S. PATENT DOCUMENTS

| | | | |
|---|---|---|---|
| 3,743,607 | 7/1973 | Sennewald et al. | 502/170 |
| 3,822,308 | 7/1974 | Kronig et al. | 560/245 |
| 4,048,096 | 9/1977 | Bissot | 502/170 |
| 4,087,622 | 5/1978 | Nakamura et al. | 560/245 |

FOREIGN PATENT DOCUMENTS 0747415 11/1966 Canada .
1215210 12/1970 United Kingdom .
1511869 5/1978 United Kingdom .

OTHER PUBLICATIONS

Chemical Abstracts 115(14):136969y (1991).
Chemical Abstracts 75(14):89050k (1971).
Chemical Abstracts 70(9):37210q (1969).
Journal of Catalysis, vol. 17, pp. 366-374, 1970 (Nakamura et al.).

*Primary Examiner*—W. J. Shine
*Assistant Examiner*—Douglas J. McGinty
*Attorney, Agent, or Firm*—E. C. Trautlein

[57] ABSTRACT

This invention provides a process for producing improved catalysts for the production of alkenyl alkanoates by the reaction of an alkene, an alkanoic acid and an oxygen-containing gas. The catalysts contain palladium, gold and a potassium promoter and are characterized by a reduced sodium content which results in increased catalyst activity. The reduced sodium content is obtained by washing the catalyst with water or with an aqueous solution of a potassium promoter after it has been impregnated with a potassium promoter.

7 Claims, 1 Drawing Sheet

ALKENYL ALKANOATE CATALYST PROCESS

This invention relates to a process for producing catalysts (hereinafter referred to as "alkenyl alkanoate catalysts") for the production of alkenyl alkanoates from alkenes, alkanoic acids and an oxygen-containing gas.

DESCRIPTION OF THE RELATED ART

Processes for producing alkenyl alkanoate catalysts are known. By way of illustration, British Patent 1,215,210 (National Distillers) discloses a process for the production of olefinically unsaturated carboxylic esters (e.g., vinyl acetate) comprising reacting an olefinically unsaturated compound, a carboxylic acid and oxygen in the presence of a catalyst containing palladium metal and platinum metal and activated with at least one alkali metal or alkaline earth metal hydroxide or organic acid salt or inorganic acid salt.

The alkenyl alkanoate catalysts of National Distillers are produced by: (1) dissolving salts of the metals in conventional solvents, (2) spraying the solutions on an inert carrier or soaking the inert carrier in the solutions, (3) removing the solvent, (4) converting the salts so deposited on the carrier to the free metals: (a) by thermal decomposition, (b) by reduction with hydrogen or (c) by reduction in suspension using aqueous alkaline formaldehyde, aqueous hydrazine or aqueous or alcoholic sodium borohydride, (5) washing the catalyst with water to remove chlorides (see the National Distillers Examples) and (6) activating the catalyst. In the National Distillers catalyst preparation procedure, there is no precipitation of the metal salts on the carrier prior to their conversion to the free metals.

The National Distillers' alkenyl alkanoate catalysts are activated with a minor amount of at least one alkali metal or alkaline earth metal hydroxide or organic acid salt or inorganic acid salt. The alkali metal or alkaline earth metal salts of weak acids, both organic and inorganic acids are stated to be especially useful as activators. Sodium, lithium, potassium, rubidium and cesium salts and mixtures thereof are stated to be most effective as activator and the use of sodium and potassium salts, e.g., sodium and potassium acetates is especially preferred. The salts may have such anions as citrate, acetate, borate, phosphate, tartrate, benzoate or aluminate. National Distillers discloses that alkali metal and alkaline earth metal hydroxides are also effective activators and that the use of halide anions should preferably be avoided, since the presence of halides is stated to deleteriously affect the synthesis reaction.

In both of the National Distillers' Examples the salts were reduced with hydrogen and washed with water to remove chlorides. Then the catalysts were treated with aqueous solutions containing both sodium acetate and potassium acetate and dried in a rotary evaporator and then under vacuum. Based on the amount of sodium acetate used, the resulting catalysts contained about 0.23 weight percent sodium. The most active catalyst of the National Distillers' Examples (i.e., the catalyst of Example 2H) is disclosed as having an activity of 8.3 grams of vinyl acetate per gram of palladium per hour (equivalent to about 165 grams of vinyl acetate per liter of catalyst per hour, assuming a catalyst density of one gram per milliliter).

As another illustration, Journal of Catalysis, volume 17, pages 366 to 374, 1970 (Nakamura et al.) discloses vinyl acetate catalysts produced by impregnating a carrier (calcined alumina) with an aqueous solution of palladium chloride, evaporating to dryness, reducing with an alkaline hydrazine hydrate solution, washing with distilled water to remove chloride ions, impregnating with a metal salt solution (e.g., a potassium or sodium acetate solution) and drying. Nakamura et al. reports that impregnating with potassium acetate results in a catalyst activity of 25 grams of vinyl acetate per hour per liter of catalyst while impregnating with sodium acetate results in a catalyst activity of 19 grams of vinyl acetate per hour per liter of catalyst.

As a further illustration, U.S. Pat. No. 3,743,607 (Sennewald et al.) discloses a process for making vinyl acetate from ethylene, acetic acid, and molecular oxygen or air in the gas phase. A mixture of these reactants is passed in contact with a supported catalyst containing metallic palladium, an alkali metal formate or acetate, and metallic gold.

The vinyl acetate catalysts of Sennewald et al. are produced by impregnating a catalyst carrier with an aqueous solution of a palladium salt and a gold salt and the resulting mixture is evaporated to dryness. The mass so obtained is introduced into an aqueous solution containing an appropriate reducing agent (e.g., hydrazine) that is capable of reducing both the palladium and gold salts to the metallic state. In the Sennewald et al. catalyst preparation procedure, there is no precipitation of the salts on the carrier prior to the reduction. Once the reduction is complete, the catalyst mass is removed from the liquid by filtration and washed with water. When the reduction is achieved by means of a reducing agent free of alkali (e.g., hydrazine), the catalyst is conveniently impregnated with an about 10% solution of sodium acetate. The formates or acetates of lithium or potassium can also be used. The catalyst is then dried and is ready for use. Sennewald et al. discloses that, in the absence of such treatment, despite the gold it contains, the catalyst is found to have a substantially lower activity (e.g., an activity of only 15 grams vinyl acetate per liter of catalyst per hour) instead of the activity of 50 to 120 grams vinyl acetate per liter of catalyst per hour disclosed in Sennewald et al. for the Sennewald et al. catalysts. Catalysts which have been reduced by means of a composition comprising sodium formate and formic acid are disclosed to be active, even if no sodium acetate has been added thereto.

Sennewald et al. states that it has unexpectedly been found that the vinyl acetate space/time yields and, more Particularly, the lifetime of the supported catalyst until regeneration thereof, can be substantially increased when the catalyst is impregnated with a solution prepared from a mixture of various acetates of sodium, potassium, rhodium or cesium instead of impregnation with a solution of a single alkali metal acetate.

The highest activity reported in the Sennewald et al. Examples is in Example 11 where a catalyst was impregnated with sodium and potassium acetate as described in Example 9 of Sennewald et al. To effect the impregnation, the catalyst was introduced into a solution of the acetates, the supernatant solution was decanted and the catalyst was dried. The catalyst so obtained in Example 11 of Sennewald et al. is reported to contain about 0.8% sodium and to have an activity of 146 grams of vinyl acetate per liter of catalyst per hour. The other Sennewald et al. Examples (including Examples 4, 5 and 12(e) where the catalysts were apparently substantially free of sodium) reported even lower catalyst activities than Example 11. The catalysts of Sennewald et al. Examples 4 and 9 were reported to have the same palladium and gold contents and almost the same activities. The catalyst of Example 4 is reported to contain 2.5% potassium (as potassium acetate) while the catalyst of Example 9 is reported to contain about 1.8% sodium (as sodium acetate).

U.S. Pat. No. 3,822,308 (Kronig et al.) discloses that particularly active supported catalysts containing palladium and gold for the production of vinyl esters from ethylene, lower carboxylic acids with 2 to 4 carbon atoms and oxygen in the gas phase at elevated temperature and at normal or elevated pressure are obtained by the following procedure: The catalyst support is treated, simultaneously or successively, with or without intermediate drying, with a solution ("Solution A") containing dissolved salts of palladium and gold and, optionally, salts of other metals, and another solution ("Solution B") containing compounds (hereinafter referred to as "precipitating agents") which are able to react on the catalyst support with the noble metal salts of the Solution A to form water-insoluble noble metal compounds which are practically free from halogen, sulphur and nitrogen. Solutions A and B (separately or in combination) are used to impregnate the catalyst support in quantities which correspond to from 10 to 110% of the absorptive capacity of the catalyst support for these solutions. The catalyst support impregnated with Solutions A and B is subjected to a time/temperature treatment such that at least 95% of the impregnated palladium and at least 95% of the impregnated gold are transformed into water-insoluble noble metal compounds. The water-insoluble noble metal compounds are largely transformed by treatment with reducing agents into the noble metals and the water-soluble compounds which are contained in the catalyst are removed by washing, before or after the reduction.

In a preferred embodiment of the Kronig et al. process, alkali metal carboxylates (especially alkali metal acetates) are applied on the catalyst before or after the treatment with reducing agents in such quantities that the catalyst, after being dried, contains from 1 to 30% by weight of alkali metal carboxylate. Examples of the alkali metal carboxylates disclosed in Kronig et al. include sodium formate, potassium acetate, sodium acetate, lithium acetate, potassium propionate and potassium butyrate.

The Kronig et al. Examples employing precipitating agents report catalyst activities markedly higher than the activities reported by National Distillers and Sennewald et al. where no precipitating agents are used. Thus, Kronig et al. Example 1 employs sodium hydroxide as a precipitating agent and potassium acetate as a promoter and reports a activity of 452 grams of vinyl acetate per hour per liter of catalyst. Kronig et al. Example 3 employs potassium carbonate as a precipitating agent and an "alkali metal acetate" as a promoter and reports that the results obtained with the catalyst were comparable to those of Kronig et al. Example 1.

U.S. Pat. No. 4, 096 (Bissot) discloses a catalyst having a specific activity of at least about 83 grams of vinyl acetate per gram of precious metal per hour measured at 150° C. The Bissot vinyl acetate catalyst consists essentially of: (1) a catalyst support having a particle diameter of from about 3 to about 7 mm and a pore volume of from about 0.2 to about 1.5 ml./g., a 10% by weight water suspension of the catalyst support having a pH of from about 3.0 to about 9.0; (2) a palladium-gold alloy distributed in a surface layer of the catalyst support, the surface layer extending less than about 0.5 mm from the surface of the support, the palladium in the alloy being present in an amount of from about 1.5 to about 5.0 grams per liter of catalyst, and the gold being present in an amount of from about 0.5 to about 2.25 grams per liter of catalyst, and (3) from about 5 to about 60 grams per liter of catalyst of alkali metal acetate. Bissot discloses that the palladium is the active catalyst metal and the gold is a catalyst promoter.

Bissot also discloses a process for preparing the Bissot catalyst. Like Kronig et al., the Bissot process involves precipitation of the metal salts on the catalyst support. The Bissot process comprises: (1) impregnating the catalyst support with aqueous solution of water-soluble palladium and gold compounds, (2) precipitating water-insoluble palladium and gold compounds on the catalyst support by contacting the impregnated catalyst support with a solution of compounds (preferably sodium metasilicate) capable of reacting with the water-soluble palladium and gold compounds to form water-insoluble palladium and gold compounds, (3) converting the water-insoluble palladium and gold compounds into palladium and gold metal on the support by treatment with a reducing agent, (4) washing the catalyst with water, (5) drying the catalyst (see Example 1 of Bissot), (6) impregnating the catalyst with an alkali metal acetate promoter (e.g., a potassium promoter), and (7) drying the catalyst.

The improvement disclosed in Bissot involves distributing the palladium and gold as an alloy in a surface layer of the catalyst support, the surface layer extending less than about 0.5 millimeter from the surface of the support. The impregnating step is carried out with an aqueous solution of palladium and gold compounds and the total volume of the solution is from about 95 to about 100% of the absorptive capacity of the catalyst support. The precipitating step in Bissot is carried out by soaking the wet catalyst support with a solution of an alkali metal silicate, the amount of alkali silicate being such that, after the alkali metal silicate solution has been in contact with the catalyst support for about 12 to 24 hours, the pH of said solution is from about 6.5 to about 9.5.

Bissot does not report the sodium content of the catalysts of the Bissot Examples. Bissot Example 1 reports that the catalyst of that Example had an activity of 560 grams of vinyl acetate per liter of catalyst per hour. In Example V below, two catalysts produced following the disclosure of Example 1 of Bissot were found to have sodium contents of 0.32 and 0.38 weight percent and activities of 551 and 535 grams of vinyl acetate per liter of catalyst per hour.

Despite the foregoing prior art processes, it is desirable to further improve the activity of alkenyl alkanoate catalysts.

SUMMARY OF THE INVENTION

This invention is based, in part, on the discovery that the activity of alkenyl alkanoate catalyst produced by the process of U.S. Pat. No. 4,048,096 is increased if, after above-described step (7) of the process of that patent, the sodium content of the catalyst is reduced by washing the catalyst with water or with an aqueous solution of a potassium promoter.

More specifically, this invention provides a process for producing a catalyst that is useful in catalyzing the reaction of an alkene, an alkanoic acid and an oxygen-containing gas to produce an alkenyl alkanoate and that comprises support particles which are capable of exchanging cations and which are impregnated with palladium, gold and a potassium promoter, said process comprising the steps of:

(a) impregnating the support particles with aqueous solutions of water-soluble palladium and gold compounds;

(b) precipitating water-insoluble palladium and gold compounds onto the support particles from such solutions using a precipitating agent;

(c) converting the precipitated water-insoluble palladium and gold compounds to palladium and gold on the support Particles using a reducing agent; and (d) washing the impregnated support with water, (e) drying the washed impregnated support, (f) further impregnating the support particles with a potassium promoter, (g) drying the support so impregnated to produce a dried catalyst containing sodium owing to the presence of sodium in one or more of the materials used in steps (a) to (f), (h) washing the dried catalyst with water or with an aqueous solution containing a potassium promoter so as to reduce the amount of sodium in the catalyst and thereby to increase the activity of the catalyst, and (i) drying the catalyst.

In the practice of the process of this invention, it is preferred to use an aqueous solution containing a potassium promoter in step (h) to avoid lowering the concentration of the potassium promoter [with which the support was impregnated in step (f)] below the desired level. Such undesirable lowering of Promoter concentration may occur if water as such is used in step (h). However, if water is used in step (h) and the promoter concentration is thereby undesirably decreased, then step (i) can be followed by step (j) which is a second potassium promoter impregnation and then by step (k) which is a third drying. In some instances, excess potassium promoter can be used in the initial potassium promoter impregnation [step (f)] to ensure that the product of step (i) has the desired level of potassium promoter even after water washing [step (h)]. The latter procedure also obviates the need for steps (j) and (k).

Without wishing to be bound by any particular theory, it is believed that the potassium promoter used in the catalyst preparation procedure of Bissot displaces at least a portion of the sodium which was bound to ion-exchange sites on the catalyst support. The source of the sodium is the starting materials (especially the precipitating agent) used in the Bissot catalyst preparation procedure. Although displaced by the potassium promoter, such sodium remains in the catalyst produced by the Bissot process as an activity-suppressing impurity. In the process of this invention, the displaced sodium is readily removed from the catalyst by merely washing the catalyst with water or with an aqueous solution containing a potassium promoter [step (h)]. Prior to its displacement by the potassium promoter in step (f), the sodium cannot be effectively removed from the catalyst by the simple water washing [i.e., as in step (d)] because the sodium is too tightly bound to the support. However, step (d) is effective in removing unbound impurities, particularly chlorides and excess reagents from steps (a) through (c).

DESCRIPTION OF THE PREFERRED EMBODIMENTS

Figure 1:
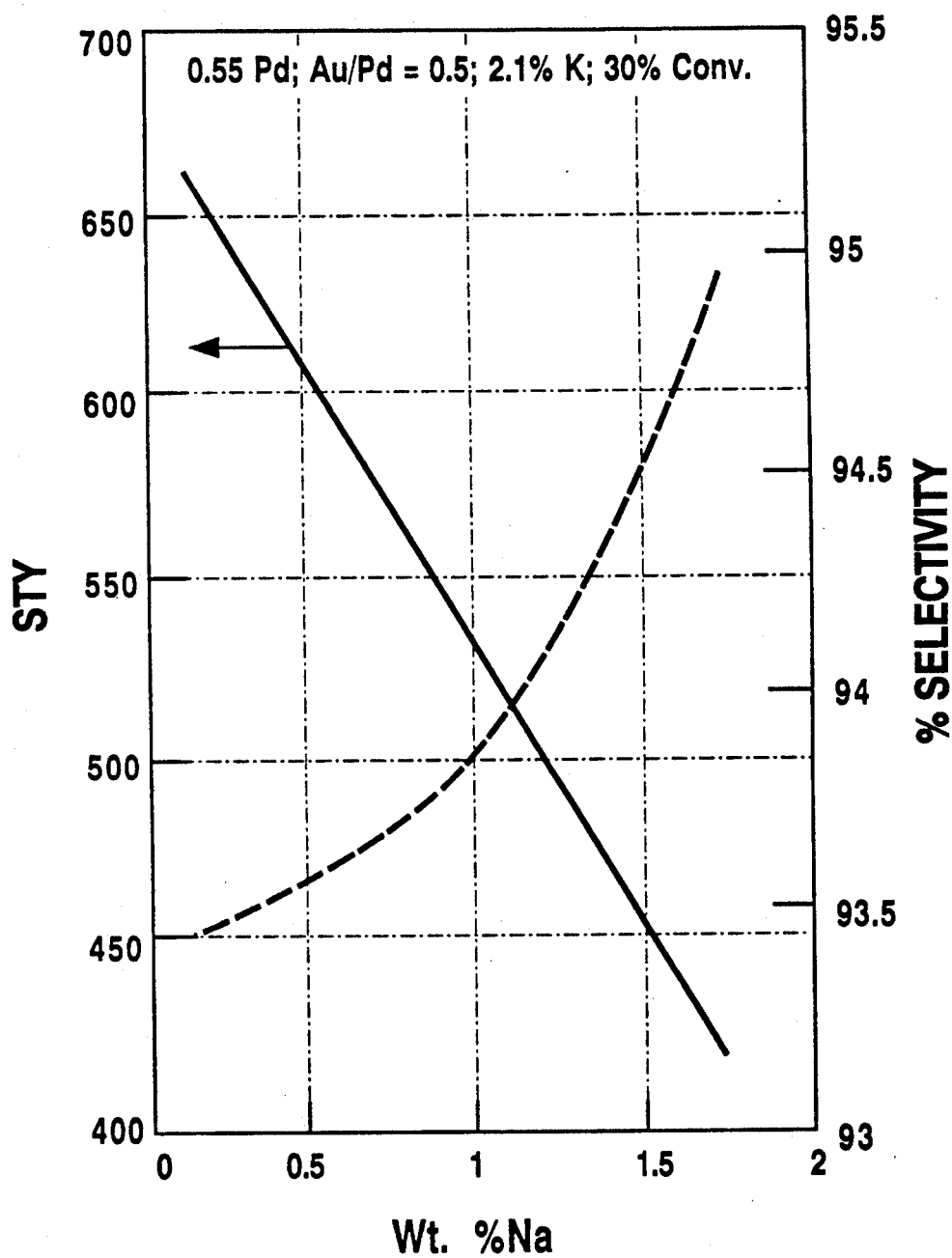
FIG. 1 shows the predicted effect of sodium on the performance of vinyl acetate catalysts produced in accordance with this invention.

The support particles used in the process of this invention are solid particulate materials that are capable of exchanging cations, that are capable of being impregnated with palladium, gold and a potassium promoter and that are inert under the conditions used to produce alkenyl alkanoates. Illustrative of such support particles are particulate silica, alumina, and silica-aluminas. Silica is the preferred support. The support preferably has a surface area from 100 to 800 square meters per gram.

The aqueous solutions of water-soluble palladium and gold compounds used in the process of this invention include aqueous solutions of any suitable palladium or gold compound such as palladium (II) chloride, sodium tetrachloropalladium (II) ($Na_2PdCl_4$), palladium (II) nitrate, palladium (II) sulfate, gold (III) chloride or auric (III) acid ($HAuCl_4$). The volume of the solution preferably corresponds to from 95 to 100% (more preferably from 98 to 99%) of the pore volume of the support.

The precipitating agents used in the process of the present invention catalysts include sodium, lithium and potassium silicates and hydroxides. The precipitating agents are preferably employed in the form of aqueous solutions containing a 1.6 to 1.8 molar excess of the precipitating agents. The volume of such solutions used is preferably just sufficient to cover the support particles.

The reducing agents used in the process of this invention include hydrazine, ethylene, formaldehyde, hydrogen and sodium borohydride. The reducing agents are preferably employed in the form of aqueous solutions containing a 50:1 (or more preferably a 10:1) molar excess of the reducing agents. If hydrogen is used, it is usually necessary to heat the catalyst to 100 to 300° C. to complete the reduction.

The potassium promoters used in the process of this invention for producing alkenyl alkanoate catalysts include potassium alkanoates and any potassium compound that is converted to a potassium alkanoate during the alkenyl alkanoate-forming reaction (i.e., the reaction of ethylene, an alkanoic acid and an oxygen-containing gas in the presence of the catalyst to produce a alkenyl alkanoate). Suitable potassium compounds include potassium acetate, bicarbonate, nitrate and (when a stable support is used) hydroxide. The promoters are preferably applied in the form of aqueous solutions.

Washing steps (d) and (h) of the process of this invention can be conducted batchwise or continuously. Continuous washing is more efficient but may not be most suitable for large scale (e.g., plant scale) catalyst production. In continuous washing, the wash liquid is slowly and continuously passed through the catalyst over a period of time (e.g., from 8 to 24 hours). In batch washing, the catalyst is contacted with the wash liquid, the mixture is allowed to stand (e.g., for from 0.5 to 2.0 hours) and the liquid and catalyst are separated. In batch washing, several such washes (e.g., from 2 to 10, or preferably from 4 to 6 washes) are often required. Temperatures from 20° C. to 80° C. and volume ratios of wash liquid to catalyst of from 2:1 to 100:1 can be used in either batch or continuous washing.

The washing of the catalyst with water or an aqueous solution containing a potassium promoter in step (h) of the process of this invention is distinct from the potassium promoter impregnation steps of prior art processes for producing alkenyl alkanoate catalysts. Such prior art impregnation steps are conducted by the incipient wetness technique or the decantation technique. In the incipient wetness technique [see the Example 5 of British Patent 1,215,210 (National Distillers)], the catalyst is contacted with the minimum amount of aqueous potassium promoter solution required to fill the pores of the support and to impregnate the catalyst with the desired amount of potassium promoter. Then the water is evaporated. No sodium can be removed from the catalyst by that technique. In the decantation technique, the catalyst (preferably dry) is immersed in a larger volume of the aqueous potassium promoter solution than is used in the incipient wetness technique. After the pores are filled with the solution, the excess solution is decanted and the catalyst is dried. Only one immersion and decantation operation is conducted and the contact time is relatively short. Hence, only a minimal amount of sodium can be removed from the catalyst by the decantation technique. Example 9 of U.S. Pat. No. 3,743,607 (Sennewald et al.) illustrates the decantation technique using a moist catalyst.

The drying of the catalyst in accordance with steps (e), (g), (i) or (k) of the process of this invention for producing alkenyl alkanoate catalysts can be conducted in any convenient manner. By way of illustration, drying can be conducted at 40° C. to 120° C. in a forced air oven for 15 to 30 hours.

The catalysts produced by the process of this invention are useful in catalyzing the reaction of an alkene, an alkanoic acid and an oxygen-containing gas to produce an alkenyl alkanoate and comprise support particles which are capable of exchanging cations and which are impregnated with precipitated and reduced palladium and gold and a potassium promoter, any sodium in the catalyst desirably being present in an amount no more than 0.3 weight percent based on the total weight of the catalyst.

It is preferred that the catalysts produced by the process of this invention are shell impregnated catalysts wherein a catalyst support has a particle diameter from about 3 to about 7 millimeters and a pore volume of 0.2 to 1.5 milliliters per gram. The palladium and gold are preferably distributed in the outermost 1.0 millimeter thick layer of the catalyst support particles. The catalysts preferably contain from about 1.4 to about 3.8 weight percent (more preferably from 2 to 3.6 weight percent) of the potassium promoter.

The catalysts produced by the process of this invention preferably have a palladium content of greater than 0.25 weight percent based on the total weight of the catalyst, more preferably greater than 0.5 weight percent based on the total weight of the catalyst and more preferably from 0.5 to 1.7 weight percent based on the total weight of the catalyst. It is preferred that the gold to palladium weight ratio of the catalyst is from 0.2 to 1.5 and, most preferably, from 0.4 to 1.2.

The catalysts produced by the process of this invention have reduced sodium contents. Preferably, the catalysts desirably contain no more than 0.3 weight percent sodium based on the weight of the catalyst. More Preferably, the catalysts contain no more than 0.2 weight percent sodium and, most preferably, the catalysts contain no more than about 0.1 weight percent sodium based on the weight of the catalyst. The amount of sodium in the catalysts will depend upon such factors as the starting materials used, the number of washes, the total volume of wash water, and the total washing time.

The alkenyl alkanoate catalyst produced by the process of this invention are characterized by their increased catalytic activity. Typically the activity of the catalysts is 5% to 25% greater (in terms of quantity of alkenyl alkanoate produced per unit of catalyst per unit time) than otherwise identical catalysts containing from over 0.3 to about 1.0 weight percent sodium. Although catalyst selectivity (i.e., the tendency to produce alkenyl alkanoates rather than by-products such as carbon dioxide) declines somewhat with decreasing sodium content, that disadvantage is more than offset by increased catalyst activity, particularly in the range of sodium contents found in commercial alkenyl alkanoate catalysts (e.g., up to about 1.0 weight percent sodium).

The process for producing alkenyl alkanoates using the above-described catalysts ("alkenyl alkanoate process") comprises reacting an alkene, an alkanoic acid, and an oxygen-containing gas in the Presence of a catalytic amount of catalyst produced by the invention described above. The alkenyl alkanoate process is preferably conducted at a temperature from 100° C. to 250° C. (and most preferably at a temperature from 140° C. to 200° C.) and at a pressure from 15 psi to 300 psi (most preferably at a pressure from 90 pounds per square inch to 150 pounds per square inch.) The alkenyl alkanoate process is preferably conducted continuously in the vapor phase.

Preferred alkanoic acid starting materials used in the alkenyl alkanoate process contain from two to four carbon atoms (e.g., acetic, propionic and butyric acid). Preferred alkene starting materials contain from two to four carbon atoms (e.g. ethylene, propylene and n-butene). Preferred products of the alkenyl alkanoate process are vinyl acetate, vinyl propionate, vinyl butyrate, and allyl acetate.

The alkenyl alkanoates produced by the alkenyl alkanoate process are known compounds having known utilities (e.g., vinyl acetate is useful in producing polyvinyl acetate).

Other processes for producing alkenyl alkanoate catalysts having reduced sodium content (and so increased catalyst activity) are described and claimed in the U.S. patent application Ser. No. 07/793,129, entitled Catalysts for Alkenyl Alkanoate Production and U.S. patent application Ser. No. 07/793,131, entitled Production of Alkenyl Alkanoate Catalysts, both filed concurrently herewith in the name of the instant applicant.

EXAMPLES

In the following Examples, the following abbreviations are used:

| Abbreviation | Meaning |
| --- | --- |
| Support I | Silica beads having an average diameter of 5 to 6 millimeters and containing about 0.1 weight percent sodium. The beads have a surface area from 150 to 200 square meters per gram and a pore volume from 0.6 to 0.7 milliliters per gram. Support I contains SiOH groups that are capable of |

-continued

| Abbreviation | Meaning |
| --- | --- |
| Catalyst I | exchanging cations. Support I is sold by Sud Chemie AG as "KA-160" The catalyst illustrating the prior art prepared in accordance with Catalyst Preparation Procedure described below using sodium metasilicate as the precipitating agent and the Column Washing Procedure. |
| Catalyst II | A larger scale (20 liter) pilot plant preparation of Catalyst I using sodium hydroxide as the precipitating agent and using the Batch Washing Procedure described below. |
| STY* | Space Time Yield (a measure of catalyst activity) expressed as grams of vinyl acetate per liter of catalyst per hour. |
| % Selectivity* | Selectivity was calculated as follows: Selectivity = 100 X (moles vinyl acetate)/(moles vinyl acetate + ½ X moles $CO_2$) |
| AA Analysis | Atomic Adsorption Spectroscopy |
| ICP | Inductively Coupled Plasma Optical Emission Spectrometry |
| VA | vinyl acetate |
| g VA/l cat/hr | Grams of vinyl acetate produced per liter of catalyst per hour |
| EtOAc | ethyl acetate |
| KOAc | potassium acetate |
| NaOAc | sodium acetate |
| % | percent by weight |
| g | grams |
| ml | milliliter |
| mm | millimeter |
| hrs | hours |
| min | minute |

*All the values for activities and selectivities reported in the Examples appearing below are based on the activities and selectivities measured twenty-six hours after full oxygen feed was reached in the Catalyst Test Method described below.

In the following Examples, the following procedures were used:

CATALYST PREPARATION PROCEDURE

A. Support I (15 g) was added to a solution of $Na_2PdCl_4$ (35.86% Pd, 0.258 g) and $HAuCl_4$ (48.95% Au, 0.094 g) dissolved in 9.0 ml of deionized water. The mixture so formed was gently agitated until all of the moisture was absorbed into the support and then was allowed to stand in a sealed flask for about one hour at room temperature so as to impregnate the support with the palladium and gold salts. The damp catalyst was covered with a solution of either sodium hydroxide (0.236 g in 28 ml water) or sodium metasilicate, $Na_2SiO_3$, (0.837 g in 28 ml water) as a precipitating agent. After mixing for a few seconds, the mixture was allowed to stand covered and undisturbed for 23 hours at room temperature to deposit water-insoluble palladium and gold compounds on the support. The palladium and gold were then reduced by the addition of 1.0 g of 85% hydrazine hydrate to the above mixture. The mixture was agitated for a few seconds and allowed to stand covered and undisturbed at room temperature for another 23 hours. The supernatant liquid was decanted from the catalyst and the catalyst was rinsed four times with water to remove the small amount of metal sludge present. The catalyst was washed thoroughly by either the Column Washing Procedure or the Batch Washing Procedure described below. The catalyst was dried on a stainless steel screen at 60° C. in a forced air oven for 20 to 24 hours. The catalyst was analyzed for potassium using AA Analysis. Then the catalyst was impregnated with the desired amount of potassium acetate in water using the impregnation technique described above for the palladium and gold salts. Then the impregnated catalyst was dried at 60° C. for 20 to 24 hours. The prior art process of U.S. Pat. No. 4,048,096 (Bissot) [i.e., above described steps (a) to (g)] is complete at this point. The process of this invention has the additional steps (h) and (i) followed by, if desired, steps (j) and (k) as illustrated below.

B. The Palladium, gold, sodium, and potassium contents in the finished catalysts were determined by ICP analyses. In most cases, sodium and potassium were also determined by AA Analyses for greater accuracy.

C. Unless otherwise noted, the foregoing procedure was used to prepare all the catalysts referred to in the following Examples. When different quantities of Support I were used, the quantities of the other starting materials used were varied correspondingly.

D. All the catalysts produced as described in the Examples appearing below were shell-impregnated (i.e., substantially all of the palladium and gold was present in a shell within 0.5mm of the surface of the beads of Support I.)

CATALYST WASHING PROCEDURES

A. Column Washing Procedure

Catalysts were washed or rewashed in a 1.24 inch o.d. × 24 inches glass chromatography column fitted with a Teflon TM stopcock. Typically 15 g of catalyst was added to the column which was then filled with the wash liquid. The stopcock was adjusted to allow the liquid to flow from the column such that about one liter passed through the catalyst at room temperature over a period of about 24 hours. After this period, the excess liquid was drained from the column and the catalyst removed and dried as described above in the Catalyst Preparation Procedure.

B. Batch Washing Procedure

Catalysts were washed in the same column apparatus described above for the Column Washing Procedure. In this variation, the column was filled with just enough wash liquid to cover the catalyst and was then allowed to stand at room temperature for a specified period. The stopcock was opened and the liquid drained. The catalyst was again covered with water or salt solution and allowed to stand as before. Washing was continued in this manner for a total of five washes. The total elapsed time was typically 8 hours. After washing, the excess liquid was drained and the catalyst removed and dried as in the Catalyst Preparation Procedure described above.

CATALYST TEST METHOD

The catalyst (2.5 g samples of 5 to 6 mm catalyst spheres) was diluted with 10.5 ml of 0.5 mm glass beads and the mixture was uniformly distributed in both legs of a 316-stainless steel U-tube reactor. The reactor had an outside diameter of ⅜ inch and an overall height of about 6 inches. An ethylene flow of 151 ml/min. was started through the reactor after which the catalyst was heated in an oven maintained at 150° C. while allowing the system to pressurize to 115 psig. After maintaining at these conditions for 1.5 hours, acetic acid vapor was added to the ethylene and the mixture was passed over the catalyst for 45 minutes. Air was added to the feed gas at a slowly increasing rate over a 45-minute period until a total flow of 105 ml./min. was reached. The catalyst was allowed to stabilize for two hours before beginning data collection. The final gas composition was ethylene:acetic acid:oxygen:nitrogen =52.9:10.7:7.7:28.7, the total gas hourly space velocity was about 3800 $hr^{-1}$, and the acetic acid liquid hourly space velocity was about 1 $hr^{-1}$. The product was analyzed by gas chromatography. The run-to-run reproducibility of the microreactors used in these experiments is about ±10 STY units.

EXAMPLE I

A. Comparative

An important step in alkenyl alkanoate catalyst preparation is the water washing step which is known to remove liberated chloride and residual starting materials. In the laboratory, catalysts are conveniently washed in a column over a 20 to 24-hour period, using about 60–80 ml of water per gram of catalyst. For practical and economic reasons, large-scale (e.g., pilot plant) preparations are washed batchwise over a much shorter time using significantly lower volumes of water per volume of catalyst washed. Catalysts made in large-scale equipment have been found to be less active than catalysts made in laboratory scale equipment. It was suspected that the activity differences were due to less efficient washing in the large-scale equipment.

Table I compares typical Performance results of laboratory prepared catalysts with catalysts prepared in large-scale equipment following the process of U.S. Pat. No. 4,048,096 (Bissot). Specifically, all the catalysts were made using the Catalyst Preparation Procedure with sodium metasilicate as the precipitating agent, except that the amounts of starting material was scaled up in the large-scale preparations and except for the differences in washing procedures. In the laboratory-scale preparations, the Column Washing Procedure was used and, in the large-scale preparations, the Batch Washing Procedure was used. The catalysts prepared using large-scale equipment include 80-liter pilot plant samples as well as samples from 260-liter equipment typical of that intended for full commercial production. The catalysts prepared using the large scale equipment typically contained about 5 to 10 weight percent more palladium than the catalysts prepared in the laboratory, yet the STY's of catalysts prepared in large-scale equipment are about 5 to 10 percent lower.

TABLE I

Activities of Laboratory-Scale And Large-Scale Catalysts Preparations

| Catalyst of Comparative Example | STY(a) | Spec. Act.(b) | % Pd(c) | % Au(c) |
|---|---|---|---|---|
| Laboratory-Scale Preparations | | | | |
| I-1 | 571(3) | 197.0 | 0.516 | 0.198 |
| I-2 | 546(3) | 188.5 | 0.516 | 0.208 |
| I-3 | 543 | 191.6 | 0.505 | 0.198 |
| I-4 | 556(2) | 181.9 | 0.510 | 0.200 |
| I-5 | 547 | 194.4 | 0.500 | 0.190 |
| I-6 | 567 | 198.0 | 0.510 | 0.200 |
| Average | 555 | 191.9 | | |
| Large-Scale Preparations | | | | |
| I-7(d) | 521 | 165.4 | 0.558 | 0.231 |
| I-8(d) | 532(2) | 172.0 | 0.554 | 0.248 |
| I-9(d) | 534(2) | 172.7 | 0.553 | 0.238 |
| I-10(d) | 521(2) | 168.5 | 0.552 | 0.237 |
| I-11(e) | 495(6) | 163.0 | 0.543 | 0.214 |
| I-12(e) | 484 | 156.5 | 0.553 | 0.223 |
| I-13(e) | 485 | 156.9 | 0.554 | 0.222 |
| I-14(e) | 528 | 173.9 | 0.589 | 0.226 |
| I-15(e) | 525 | 172.8 | 0.568 | 0.217 |
| I-16(e) | 468 | 154.1 | 0.536 | 0.204 |
| I-17(e) | 489(2) | 155.5 | 0.562 | 0.213 |
| I-18(e) | 520 | 165.1 | 0.564 | 0.212 |
| I-19(e) | 479 | 149.6 | 0.568 | 0.203 |
| Average | 497 | 160.6 | | |

(a)STY = Space Time Yield, g VA/l cat/hr, value in parentheses is the number of runs averaged; (b)Specific Activity, g VA/g Pd/hr; (c)Wt % Pd and Au as determined by ICP analyses; (d)80-liter pilot plant run; (e)260-liter plant-scale run.

B. Invention

The data in Table I shows that the catalysts made on a large scale had lower activities than the catalysts made on a laboratory scale. To determine whether insufficient washing accounted for the lower activity of the catalysts made on a large scale, four of the catalysts made in large scale equipment (i.e., I-7, I-9, I-12 and I-17 of Table I) were rewashed (step (h) of the process of this invention) with water using the Column Washing Procedure and then dried [step (i)of the process of this invention]. A fifth catalyst was prepared on a laboratory scale using the Catalyst Preparation Procedure and the Batch Washing Procedure and a portion of this catalyst was rewashed with water (step (h) of the process of this invention) using the Column Washing Procedure and then dried [step (i) of the process of this invention]. Each of the five rewashed and redried catalysts was reimpregnated (step (j) of the process of this invention) with 5% potassium acetate to replace the potassium acetate assumed to have been removed during the rewashing and dried again [step (k) of the process of this invention]. The results are shown in Table II and indicate that in every instance rewashing improved activity by 5 to 10 percent.

TABLE II

Effect of Rewashing on Catalyst Activity

| No. | Catalyst | Rewashed | STY | % Change |
|---|---|---|---|---|
| Large Scale Preparations | | | | |
| 1* | I-7 | No | 521 | — |
| 2 | I-7 | Yes | 557 | +7 |
| 3* | I-9 | No | 534(2) | — |
| 4 | I-9 | Yes | 566 | +6 |
| 5* | I-12 | No | 484 | — |
| 6 | I-12 | Yes | 537 | +11 |
| 7* | I-17 | No | 489(2) | — |
| 8 | I-17 | Yes | 524 | +5 |
| Laboratory Preparation | | | | |
| 9* | | No | 508 | — |
| 10 | | Yes | 561 | +10 |

*Comparative Examples

EXAMPLE II

In the experiments described in Example I, it had been assumed that the rewashing (step (h) of the process of this invention) had also removed all the potassium acetate. Hence, in those experiments, potassium acetate had been reapplied (step (j) of the process of this invention) after the rewash in an amount equal to that used in the initial impregnation of the catalysts. The assumption made in connection with Example I was checked with another series of eight catalysts having varying potassium loadings. Analytical results obtained before and after rewashing are shown in Table III for these eight catalysts (Catalysts II-1 to II-8). These analytical results show that rewashing as described in Example I above did not, in fact, remove all the potassium acetate. The results shown in Table III indicate that about 0.9 weight percent potassium consistently remained in the catalyst after rewashing. It is believed that the potassium is bound to the support by an ion exchange mechanism.

TABLE III

Rewashing vs KOAc Removal

| Catalyst | Wt % K | | |
|---|---|---|---|
| | Original | Rewashed(a) | Difference |
| II-1 | 2.80 | 3.67 | 0.86 |
| II-2 | 1.50 | 2.33 | 0.83 |
| II-3 | 1.40 | 2.27 | 0.87 |
| II-4 | 1.40 | 2.35 | 0.95 |
| II-5 | 2.70 | 3.51 | 0.81 |
| II-6 | 1.40 | 2.35 | 0.95 |
| II-7 | 2.90 | 3.64 | 0.73 |
| II-8 | 2.80 | 3.68 | 0.87 |
| | | Average | 0.86 |
| | | % RSD(b) | 8.30 |

(a)After reimpregnation with the same wt % KOAc as was present in the original catalyst.
(b)RSD is the Relative Standard Deviation.

EXAMPLE III

In view of the findings shown in Table III, two of the rewashed catalysts shown in Table II were analyzed before reapplication of potassium acetate. Results, shown below, were generally consistent with those in Table III.

| Rewashed Catalyst | % K Retained |
|---|---|
| I-12 | 0.88 |
| I-17 | 1.19 |

As a consequence, the potassium loadings of all the rewashed catalysts reported in Table II were probably about 0.8 to 1.2% higher than anticipated. The higher than the desired potassium levels would be expected to decrease catalyst activity. This data suggests that activity improvements even greater than the observed 5-10% shown in Table II would be possible with proper (lower) final potassium loadings. This was confirmed when the amount of potassium added after rewashing was only the amount required to achieve the original loading as shown by Runs III-1 to III-7 below.

Comparative Run III-1: A 2.5 g portion of Catalyst II was evaluated for vinyl acetate production giving the result reported in Table IV. Portions of this catalyst were rewashed as described in Runs III-2 and III-3 below.

Run III-2: Three 50-g portions of catalyst from Run III-1 were each washed using the Column Washing Procedure and then analyzed for potassium which gave a potassium value of 0.92 wt. %. A 15-g sample of the catalyst was reimpregnated with 0.469 g of potassium acetate in 9.0 ml of water, then dried 18 hrs at 60° C. The analysis and test results for the catalyst are Provided in Table IV.

Run III-3: The procedure of Run III-2 above was used, except that four samples of Catalyst II were used and each portion (200g) was washed with 2 gallons of water over a 48-hr period using the Column Washing Procedure. The potassium level was determined to be 0.86% after combining the washed material. A 15 g sample was impregnated with a solution of 0.556 g of potassium acetate in 9.0 ml of water then dried for 24 hrs at 60° C. The analysis and test results on the catalyst are shown in Table IV.

Comparative Run III-4: This catalyst was prepared using the Catalyst Preparation Procedure, except that the concentrations of the palladium and gold salts in the impregnation solution and the other starting materials were adjusted to give the loadings shown in Table IV. Evaluation was done using the Catalyst Test Method, except that only 0.75 grams of catalyst were used. The analysis and test results are shown in Table IV.

Run III-5: A 2.75 g portion of the catalyst from Run III-4 was washed using the Column Washing Procedure using 500 ml of water over 24 hours. After drying, the catalyst was impregnated with sufficient potassium acetate to give about 3% potassium in the finished catalyst. Evaluation was done using the Catalyst Test Method, except that only 0.75 grams of catalyst were used. The analysis and test results are shown in Table IV.

Comparative Run III-6: This catalyst was prepared as per Run III-4 above, except that the concentrations of the palladium and gold salts in the impregnation solution and the other starting materials were adjusted to give the loadings shown in Table IV. Evaluation was done using the Catalyst Test Method, except that only 0.75 grams of catalyst were used. The analysis and test results on the catalyst are provided in Table IV.

Run III-7: A sample of catalyst from Run III-6 was rewashed with water using the Column Washing Procedure. Evaluation was done using the Catalyst Test Method described above, except that only 0.75 grams of catalyst were used. The analysis and test results on the catalyst are provided in Table IV.

TABLE IV

Effect of Rewashing at Constant Potassium Loading(a)

| Run | % Pd | % Au | % KOAc | % Na | Re-washed | STY | % Change |
|---|---|---|---|---|---|---|---|
| III-1* | 0.55 | 0.22 | 5.8 | 0.45 | No | 565 | — |
| III-2 | 0.55 | 0.22 | 5.3 | 0.14 | Yes | 615 | +9 |
| III-3 | 0.5 | 0.22 | 5.8 | 0.12 | Yes | 642 | +14 |
| III-4* | 0.56 | 0.46 | 7.6 | 0.42 | No | 734(b) | — |
| III-5 | 0.56 | 0.46 | 7.6 | 0.17 | Yes | 850(b) | +15 |
| III-6* | 1.02 | 0.46 | 7.2 | 0.48 | No | 967(b) | — |
| III-7 | 1.02 | 0.47 | 7.7 | 0.17 | Yes | 1141(b) | +18 |

(a)The Column Washing Procedure was used both in the original preparations and in rewashing.
(b)This catalyst was tested at low conversion which accounts for the exceptionally high STY observed for this metal loading.
*Comparative Examples.

On the basis of the results described above, studies were conducted to determine if other impurities might account for the described effects. Comparison of ICP analytical data from the original catalysts and their rewashed versions revealed significant differences in sodium content but no significant differences in other impurities were observed.

EXAMPLE IV

To test the effect of sodium on catalyst activity, a series of experiments (runs) were conducted where sodium was varied and the potassium level was held constant. In another series of experiments (runs) the sodium to potassium ratio was varied while keeping the total moles of alkali constant. The results of both series of experiments are shown in Table V and the results confirm that increasing levels of sodium do, in fact, result in diminished activity.

In Run 2 of Table V, a rewashed catalyst which was impregnated with a level of sodium similar to that in the original unwashed version (Run 4 of Table V) showed an appreciably higher activity. This suggests that another detrimental impurity may also be removed by rewashing.

TABLE V
Effect of Sodium on Catalyst Performance

| Run No. | % K | % Na | STY | % Selectivity |
|---|---|---|---|---|
| Constant K content % varied Na content(a) | | | | |
| 1 | 2.24 | 0.117 | 642 | 93.1 |
| 2 | 2.22 | 0.457 | 609 | 93.5 |
| 3 | 2.18 | 0.912 | 540 | 94.1 |
| 4 | 2.31 | 0.453 | 563 | 93.4 |
| Varied Na/K at constant moles alkali(b) | | | | |
| 1 | 2.21 | 0.435 | 616 | 93.6 |
| 2 | 1.77 | 0.705 | 584 | 94.0 |
| 3 | 0.77 | 1.300 | 501 | 94.2 |

(a)Column rewashed Catalyst II was reimpregnated with KOAc and NaOAc solutions.
(b)Prepared by appropriate addition of KOAc and NaOAc to subsamples of a master batch of Catalyst I.

EXAMPLE V

The effect of sodium on the performance of vinyl acetate catalysts was studied using statistically designed experiments and models were obtained which are useful in predicting the performance of the vinyl acetate catalysts produced by the process of this invention as well as vinyl acetate catalysts produced by the processes of the two above-mentioned U.S. patent applications filed concurrently herewith. The models predict catalyst activity and selectivity as a function of sodium content, palladium loading, gold to palladium weight ratio, potassium content and catalyst weight. These models and the data from which they were generated are shown in Tables VI and VII respectively.

Because the degree of conversion has a major effect on both catalyst productivity and selectivity, meaningful comparisons of catalyst variables can only be done at constant conversion. In order to predict the effects of catalyst composition at constant conversion, the Oxygen Conversion Model in Table VI was rearranged to express catalyst weight as a function of the palladium content, gold/palladium ratio, potassium content, sodium content and conversion. This catalyst weight term was then used to replace the catalyst weight terms in the STY and Selectivity models. The predicted effects of increasing sodium content on vinyl acetate catalyst activity and selectivity are plotted in FIG. 1.

The abbreviations used in Tables VI and VII have the following meanings:

| | |
|---|---|
| Pd | Weight percent palladium in the catalyst |
| Au/Pd | Weight ratio of gold to palladium in the catalyst |
| Cat. Wt | Catalyst weight in grams |
| K | Weight percent potassium in the catalyst |
| Na | Weight percent sodium in the catalyst |
| STY | Space time yield in grams of vinyl acetate per liter of catalyst per hour |
| $R^2$ | Correlation coefficients which are indicative of the quality of fit of the data to the models |
| RSD | Relative standard derivation |
| EtOAc By-Product Rate | Production of ethyl acetate in moles/ kilogram of catalyst/hour |
| % Heavies By-Products in VA | Heavy by-products expressed as a weight percent of the vinyl acetate produced. Heavies by-products are defined as all products which elute after acetic acid in the gas chromatographic analytical procedure. |

Table VIII shows the effect of varying sodium on catalyst activity as predicted by the models in Table VI.

TABLE VI
MODELS RELATING PERFORMANCE TO CATALYST COMPOSITION(a)

Part A

$O_2$ Conversion to Vinyl Acetate = $100/(1 + e^{Z1})$

Where Z1 = 0.507 − 1.907(% Pd-0.743) − 0.863(Au/Pd-0.584) + 0.109(% K-2.43) + 0.459(% Na-0.502) −
(19.6) (8.1) (4.5) (7.0)
.913(Cat. Wt.-1.91) + 1.438(% Pd-0.743)(Au/Pd-0.584) + 0.551(Au/Pd-0.584)(Cat. Wt.-1.91) +
(29.8) (3.9) (5.1)
1.438(% Pd-0.743)$^2$ + 2.779(Au/Pd-0.584)$^2$ + 1.384(% K-2.43)$^2$ + 0.284(Cat Wt. −1.91)$^2$
(3.1) (4.2) (4.4) (6.5)

$R^2 = 0.988$
RSD = 0.103

Part B

Activity(STY) = $e^{Z2}$

Where Z2 = 6.707 + 0.942(% Pd-0.743) + 0.334(Au/Pd-0.584) − 0.194(% Na-0.502) − 0.123(Cat. Wt.-1.91) −
(13.6) (5.6) (4.0) (8.1)
1.438(% Pd-0.743)$^2$ − 0.128(% K-2.43)$^2$
(4.3) (5.6)

$R^2 = 0.922$
RSD = 0.079

Part C

Selectivity To Vinyl Acetate = $100 - e^{Z3}$

Where Z3 = 1.9 + 0.457(% Pd-0.743) − 0.118(% K-2.43) − 0.095(% Na-0.502) + 0.121(Cat. Wt.-1.91) +
(17.4) (12.7) (3.5) (14.8)
0.186(% Pd-0.743)(Cat. Wt.-1.91) − 0.254(Au/Pd-0.584)(% K-2.43) − 0.0525(% K-2.43)(Cat. Wt.-1.91) −
(5.9) (6.3) (4.6)
0.164(% Na-0.502)(Cat. Wt.-1.91) + 0.038(% K-2.43)$^2$
(4.1) (3.2)

$R^2 = 0.956$
RSD = 0.034

Part D

EtOAc By-Product Rate = $e^{Z4}$

Where Z4 = −3.640 + 0.9175(% Pd-0.743) − 1.135(Au/Pd-0.584) − 0.2189(Cat. Wt.-1.91) − 0.3743(% Na-0.502) −
(7.5) (10.7) (8.1) (6.4)
0.267(% K-2.43)$^2$ − 2.428(% Pd-0.743)$^2$
(7.2) (4.1)

$R^2 = 0.872$
RSD = 0.142

TABLE VI-continued
MODELS RELATING PERFORMANCE TO CATALYST COMPOSITION(a)

Part E

% Heavies By-Products in VA = $e^{Z5}$(b)

Where $Z5 = 0.280 + 0.441(\text{Au/Pd}-0.584) - 0.254(\% \text{ K}-2.43) - 0.0694(\text{Cat. Wt.}-1.91)$  $R^2 = 0.797$
             (5.2)                (10.5)            (3.1)                               RSD = 0.119

(a) Values in parentheses beneath the regression equations are the observed T-ratios.
(b) Based on the amount of vinyl acetate produced.

TABLE VII
DESIGN DATA(a)

| No. | % Pd | Au/Pd | % K | % Na | Cat Wt. | % O₂ Conv | STY | % Selectivity |
|---|---|---|---|---|---|---|---|---|
| 1 | 0.80 | 0.70 | 2.23 | 0.51 | 1.64 | 34.4 | 897.6 | 93.2 |
| 2 | 0.80 | 0.70 | 2.23 | 0.51 | 1.65 | 37.1 | 941.5 | 92.9 |
| 3 | 0.80 | 0.70 | 2.23 | 0.51 | 1.65 | 34.8 | 923.3 | 93.2 |
| 4 | 1.05 | 0.91 | 3.67 | 0.26 | 0.73 | 16.1 | 1181.7 | 94.4 |
| 5 | 0.57 | 0.46 | 2.33 | 0.14 | 0.73 | 7.1 | 759.2 | 94.6 |
| 6 | 0.54 | 0.89 | 2.27 | 0.16 | 2.50 | 44.9 | 727.4 | 92.5 |
| 7 | 1.13 | 0.96 | 2.35 | 0.18 | 0.75 | 21.0 | 1262.4 | 94.1 |
| 8 | 0.52 | 0.44 | 3.51 | 0.17 | 0.76 | 5.8 | 553.2 | 94.5 |
| 9 | 1.14 | 0.46 | 2.35 | 0.19 | 2.50 | 66.1 | 912.3 | 89.7 |
| 10 | 0.53 | 0.91 | 3.64 | 0.14 | 2.51 | 32.7 | 595.0 | 94.4 |
| 11 | 1.05 | 0.47 | 3.68 | 0.18 | 2.50 | 55.7 | 847.4 | 92.1 |
| 12 | 1.08 | 0.87 | 2.80 | 0.73 | 0.76 | 17.5 | 1158.0 | 93.8 |
| 13 | 0.52 | 0.46 | 1.50 | 0.37 | 0.72 | 6.6 | 569.0 | 94.0 |
| 14 | 0.52 | 0.85 | 1.40 | 0.50 | 2.50 | 38.4 | 587.4 | 91.5 |
| 15 | 1.08 | 0.94 | 1.40 | 0.54 | 0.74 | 19.3 | 1111.7 | 92.1 |
| 16 | 0.55 | 0.42 | 2.70 | 0.44 | 0.76 | 5.9 | 617.2 | 94.3 |
| 17 | 1.10 | 0.45 | 1.40 | 0.59 | 2.54 | 57.7 | 769.9 | 89.7 |
| 18 | 0.55 | 0.91 | 2.90 | 0.40 | 2.54 | 34.7 | 629.5 | 94.1 |
| 19 | 1.09 | 0.47 | 2.80 | 0.50 | 2.52 | 56.6 | 865.0 | 91.5 |
| 20 | 0.82 | 0.70 | 2.12 | 0.49 | 1.63 | 35.2 | 901.9 | 93.0 |
| 21 | 0.82 | 0.70 | 2.12 | 0.49 | 1.62 | 35.7 | 925.7 | 92.9 |
| 22 | 0.78 | 0.65 | 2.12 | 0.53 | 2.52 | 50.6 | 793.2 | 92.2 |
| 23 | 0.78 | 0.65 | 2.12 | 0.53 | 1.63 | 33.3 | 884.2 | 93.4 |
| 24 | 1.07 | 0.83 | 2.93 | 0.69 | 2.53 | 51.8 | 822.1 | 92.5 |
| 25 | 0.53 | 0.36 | 2.96 | 0.44 | 2.52 | 28.5 | 506.7 | 93.4 |
| 26 | 1.07 | 0.82 | 1.47 | 0.56 | 2.50 | 54.3 | 709.7 | 88.7 |
| 27 | 1.07 | 0.82 | 1.47 | 0.56 | 2.51 | 52.4 | 701.7 | 89.3 |
| 28 | 0.56 | 0.82 | 3.02 | 0.42 | 0.75 | 7.7 | 733.8 | 95.0 |
| 29 | 1.02 | 0.46 | 2.88 | 0.48 | 0.75 | 14.1 | 966.6 | 93.8 |
| 30 | 0.54 | 0.44 | 1.51 | 0.36 | 2.50 | 29.6 | 483.5 | 92.7 |
| 31 | 0.54 | 0.80 | 1.48 | 0.50 | 0.75 | 10.8 | 763.7 | 94.0 |
| 32 | 1.08 | 0.43 | 1.47 | 0.63 | 0.75 | 13.1 | 889.6 | 93.2 |
| 33 | 0.80 | 0.66 | 2.12 | 0.92 | 1.64 | 33.0 | 871.5 | 93.2 |
| 34 | 0.80 | 0.66 | 2.12 | 0.92 | 1.62 | 32.3 | 866.6 | 93.5 |
| 35 | 1.13 | 0.62 | 2.10 | 0.59 | 1.62 | 43.1 | 1066.2 | 92.4 |
| 36 | 0.41 | 0.61 | 2.20 | 0.37 | 1.64 | 21.3 | 621.8 | 94.2 |
| 37 | 0.76 | 0.87 | 2.10 | 0.55 | 1.62 | 33.3 | 881.8 | 93.7 |
| 38 | 0.76 | 0.34 | 2.10 | 0.45 | 1.65 | 27.5 | 734.0 | 93.4 |
| 39 | 0.77 | 0.61 | 2.10 | 0.52 | 0.43 | 9.9 | 1246.7 | 93.7 |
| 40 | 0.77 | 0.61 | 2.10 | 0.52 | 2.86 | 56.9 | 745.8 | 91.7 |
| Supplemental Data(b) | | | | | | | | |
| 41 | 0.56 | 0.39 | 2.19 | 0.44 | 2.54 | 36.0 | 607.8 | 93.5 |
| 42 | 0.57 | 0.39 | 2.19 | 0.15 | 2.54 | 38.4 | 612.0 | 92.7 |
| 43 | 0.54 | 0.39 | 3.38 | 0.68 | 2.54 | 25.8 | 482.8 | 94.1 |
| 44 | 0.55 | 0.39 | 3.38 | 0.28 | 2.54 | 30.9 | 545.9 | 93.5 |
| 45 | 0.56 | 0.39 | 2.79 | 0.28 | 2.54 | 36.4 | 605.5 | 93.4 |
| 46 | 0.56 | 0.39 | 2.79 | 0.16 | 2.54 | 37.2 | 610.9 | 92.9 |
| 47 | 0.54 | 0.39 | 2.79 | 0.96 | 2.54 | 27.4 | 493.2 | 93.8 |
| 48 | 0.54 | 0.39 | 3.62 | 0.36 | 2.54 | 27.2 | 492.4 | 93.7 |
| 49 | 0.57 | 0.39 | 1.95 | 0.20 | 2.54 | 35.3 | 571.0 | 92.9 |
| 50 | 0.54 | 0.39 | 3.70 | 0.39 | 2.54 | 27.1 | 483.8 | 93.9 |
| 51 | 0.55 | 0.39 | 2.12 | 1.25 | 2.54 | 27.4 | 494.1 | 94.1 |
| 52 | 0.50 | 0.39 | 3.95 | 2.39 | 2.54 | 13.4 | 283.9 | 94.3 |
| 53 | 0.56 | 0.39 | 2.25 | 0.50 | 2.54 | 33.6 | 609.3 | 93.5 |
| 54 | 0.57 | 0.39 | 2.25 | 0.12 | 2.54 | 34.9 | 641.5 | 93.1 |
| 55 | 0.55 | 0.39 | 2.25 | 1.01 | 2.54 | 28.7 | 540.0 | 94.1 |

(a) Unless otherwise indicated, the palladium and gold values were determined by ICP and the sodium and potassium values were determined by Atomic Absorption Analysis.
(b) The catalysts were prepared by addition of sodium and potassium acetates to the catalyst of Example III (Runs III-2 and III-3) above. Reported compositions are calculated from the analysis of this catalyst and the quantities of sodium and potassium acetate added.

TABLE VIII
Predicted Effect of Sodium on Catalyst* Activity

| % Na | STY | % Improvement** |
|---|---|---|
| 0.1 | 665 | 0.0 |
| 0.2 | 649 | 2.5 |
| 0.3 | 633 | 5.1 |
| 0.4 | 618 | 7.6 |
| 0.5 | 603 | 10.3 |
| 0.6 | 581 | 14.5 |
| 0.7 | 574 | 15.9 |
| 0.8 | 560 | 18.8 |
| 0.9 | 546 | 21.8 |

*For a catalyst composition set at: 0.58% Pd, Au/Pd = 0.45 and 2.2% K and an oxygen conversion set at 35%.
**Predicted percent change in STY resulting from decrease in sodium content from amount shown in first column to 0.1%.

COMPARATIVE EXAMPLE VI

The procedure of Example 1 of U.S. Pat. No. 4,048,096 (Bissot) was repeated as follows: Two preparations Runs 1 and 2) were made, each employing 15 g of Support I, 0.315 g of $Na_2PdCl_4$, 0.085 g of $HAuCl_4$, 0.585 g of $Na_2SiO_3 \cdot 9H_2O$, 0.59 g of 85% hydrazine hydrate, and 0.823 g of potassium acetate. Since the exact washing procedure is not disclosed in Example 1 of Bissot, the catalyst of Run 1 was washed using the Column Washing Procedure for 16 hours using 23 ml of $H_2O$ per gram of catalyst. The catalyst of Run 2 was similarly washed but with 31 ml of $H_2O$ per gram of catalyst. The catalysts of Runs 1 and 2 were analyzed by ICP for palladium and gold and by AA Analysis for potassium and sodium. The experimental error of the sodium determination is estimated to be about ±0.01 relative percent. The catalyst of Run 1 was analyzed in duplicate. The results are shown in Table IX.

TABLE IX

| Run | % Pd | % Au | % K | % Na | STY | Selectivity |
|---|---|---|---|---|---|---|
| Run 1 | 0.544 | 0.201 | 2.34 | 0.32 | 550 | 93.9 |
| Run 1 | 0.556 | 0.204 | 2.35 | 0.32 | | |
| Run 2 | 0.552 | 0.195 | 2.34 | 0.38 | 535 | 93.7 |
| Bissot | 0.578* | 0.242* | 2.08* | — | 560** | 93** |

*Calculated based on the data in Example 1 of Bissot
**Disclosed in Example 1 of Bissot

EXAMPLE VII

The measured activities of three commercial catalysts (Catalysts X, Y and Z) are shown in Table X. In Table X, The measured activities of Catalysts X and Y are compared to the predicted activities of catalysts of this invention having the same composition ("Model Catalysts"). The predicted activities were determined from the models of Table VI and assuming a 0.15% level of sodium. The Model Catalysts had markedly higher predicted activities. A similar comparison could not be made for catalyst Z because its composition is outside the range of the models of Table VI.

Catalyst X was prepared using the Catalyst Preparation Procedure. The preparation of Catalyst X differed from the preparation of Catalyst Y in that, in the preparation of Catalyst Y: (1) the catalyst was dried before precipitation and (2) the precipitating agent used was sodium hydroxide rather than sodium metasilicate. The reduction, washing, drying and potassium acetate impregnation steps were the same for both catalyst preparations.

With reference to Catalyst Y, the suffixes A, B and C in Table X denote different preparations ("lots") of nominally the same catalyst and, with respect to Catalyst Y and Z, the suffixes 1 and 2 denote duplicate analyses of different samples from the same lot of the catalysts.

Catalyst Z has a high palladium content and uses a cadmium co-catalyst rather than gold. Cadmium is significantly more toxic than gold. In addition, catalyst Z is prepared by a process substantially different from the process of this invention. That is, Catalyst Z is prepared by impregnating a support with a solution of palladium, cadmium and potassium acetates and drying. There are no precipitation, reduction or washing steps in the process used to produce Catalyst Z.

TABLE X

|  | % Pd | % Au | % Cd | % K | % Na | STY |
|---|---|---|---|---|---|---|
| Catalyst X* | 0.53 | 0.22 | 0 | 2.36 | 0.54 | 272 |
| Model Catalyst | 0.53 | 0.22 | 0 | 2.36 | 0.15 | 589 |
| Catalyst YA-1* | 0.49 | 0.19 | 0 | 2.29 | 0.60 | 360 |
| Model Catalyst | 0.49 | 0.19 | 0 | 2.29 | 0.15 | 546 |
| Catalyst YA-2* | 0.49 | 0.19 | 0 | 2.31 | 0.60 | 360 |
| Model Catalyst | 0.49 | 0.19 | 0 | 2.31 | 0.15 | 545 |
| Catalyst YB* | 0.63 | 0.24 | 0 | 2.27 | 0.70 | 386 |
| Model Catalyst | 0.63 | 0.24 | 0 | 2.27 | 0.15 | 669 |
| Catalyst YC-1* | 0.61 | 0.24 | 0 | 2.24 | 0.69 | 395 |
| Model Catalyst | 0.61 | 0.24 | 0 | 2.24 | 0.15 | 653 |
| Catalyst YC-2* | 0.61 | 0.26 | 0 | 2.18 | 0.70 | 395 |
| Model Catalyst | 0.61 | 0.26 | 0 | 2.18 | 0.15 | 658 |
| Catalyst Z-1* | 2.16 | 0 | 1.88 | 1.89 | 0.08 | 685 |
| Model Catalyst | Outside range of models | | | | | |
| Catalyst Z-2* | 2.16 | 0 | 1.89 | 1.92 | 0.09 | 685 |
| Model Catalyst | Outside range of models | | | | | |

*Comparative Catalysts

What is claimed is:

1. A process for producing a catalyst that is useful in catalyzing the reaction of an alkene, an alkanoic acid and an oxygen-containing gas to produce an alkenyl alkanoate and that comprises support particles which are capable of exchanging cations and which are impregnated with palladium, gold and a potassium promoter selected form the group consisting of potassium alkanoates and any potassium compound that is converted to a potassium alkanoate during said reaction, said process comprising the steps of:
   (a) impregnating the support particles with aqueous solutions of water-soluble palladium and gold compounds;
   (b) precipitating water-insoluble palladium and gold compounds onto the support particles from such solutions using a precipitating agent;
   (c) converting the precipitated water-insoluble palladium and gold compounds to palladium and gold on the support particles using a reducing agent; and
   (d) washing the impregnated support with water,
   (e) drying the washed impregnated support,
   (f) further impregnating the support particles with said potassium promoter,
   (g) drying the support so impregnated to produce a dried catalyst containing sodium owing to the presence of sodium in one or more of the materials used in steps (a) to (f),
   (h) washing the dried catalyst with water or with an aqueous solution containing said potassium promoter so as to reduce the amount of sodium in the catalyst and thereby to increase the activity of the catalyst, and
   (i) drying the catalyst.

2. A process as claimed in claim 1 wherein step (i) is followed by step (j) which is a second potassium promoter impregnation and by step (k) which is a third drying.

3. A process as claimed in claim 1 wherein sufficient potassium acetate is used in the initial potassium promoter impregnation [step (f)] to ensure that the product of step (i) has the desired amount of the potassium promoter.

4. A process as claimed in claim 1 wherein an aqueous solution containing a potassium promoter is used in step (h) so that the catalyst produced in step (i) has the desired amount of the potassium promoter.

5. A process as claimed in claim 1 wherein the catalyst produced by the process has a sodium content of no more than 0.3 weight percent based on the weight of the catalyst.

6. A process as claimed in claim 1 wherein the catalyst produced by the process has a sodium content of no more than 0.2 weight percent based on the weight of the catalyst.

7. A process as claimed in claim 1 wherein the catalyst produced by the process has a sodium content of no more than 0.1 weight percent based on the weight of the catalyst.

* * * * *